United States Patent [19]

Koebernick

[11] Patent Number: 4,611,058

[45] Date of Patent: Sep. 9, 1986

[54] PROCESS FOR THE PREPARATION OF 1,5-DIDESOXY-1,5-IMINO-D-GLUCITOL AND N-DERIVATIVES THEREOF

[75] Inventor: Wolfgang Koebernick, Wuppertal, Fed. Rep. of Germany

[73] Assignee: Bayer Aktiengesellschaft, Leverkusen, Fed. Rep. of Germany

[21] Appl. No.: 734,362

[22] Filed: May 14, 1985

Related U.S. Application Data

[63] Continuation of Ser. No. 558,669, Dec. 6, 1983, abandoned, which is a continuation of Ser. No. 331,335, Dec. 16, 1981, abandoned.

[30] Foreign Application Priority Data

Dec. 30, 1980 [DE] Fed. Rep. of Germany ....... 3049446

[51] Int. Cl.[4] ........................................... C07D 211/46
[52] U.S. Cl. .................................... 546/242; 536/4.1; 536/18.7
[58] Field of Search ......................................... 546/242

[56] References Cited

U.S. PATENT DOCUMENTS 2,898,379  8/1959  Chamberlain et al. ............. 568/813
4,220,782  9/1980  Stoltefuss ............................ 546/242

OTHER PUBLICATIONS

Chemical Abstracts, 93: 47104x (1980) [Ger. Offen. 2,830,469, Stoltefuss, 1/24/80].

Primary Examiner—Richard A. Schwartz
Attorney, Agent, or Firm—Sprung, Horn, Kramer & Woods

[57] ABSTRACT

The invention relates to a process for preparing 1,5-didesoxy-1,5-imino-D-glucitol (desoxynojirimicin) and N-derivative thereof, which are known to be powerful inhibitors for α-glycosidases. The process of the invention involves reducing with a complex borohydride, a 6-amino-6-desoxy-L-sorbose.

9 Claims, No Drawings

PROCESS FOR THE PREPARATION OF 1,5-DIDESOXY-1,5-IMINO-D-GLUCITOL AND N-DERIVATIVES THEREOF

This is a continuation of application Ser. No. 558,669, filed 12/6/83, now abandoned, which is a continuation of Ser. No. 331,335 filed 12/16/81 now abandoned.

The present invention relates to an unobvious process for the production of 1,5-didesoxy-1,5-imino-D-glucitol (desoxynojirimicin) and N-derivatives thereof.

These compounds are powerful inhibitors for α-glycosidases, particularly for disaccharidases (see DE-OS (German Published Specification) No. 2,758,025). The compound which is unsubstituted at the nitrogen is known in the literature as desoxynojirimicin.

It is known that 1,5-didesoxy-1,5-imino-D-glucitol is obtained if 6-amino-6-desoxy-L-sorbose is hydrogenated in aqueous solution with a platinum catalyst, according to Adams (H-Paulsen, J. Sangster and K. Heyns, chem. Ber. 100 (1967) 802 ).

The use of the very labile free base 6-amino-6-desoxy-L-sorbose is disadvantageous in this process. A substituted pyridine derivative is always formed from the free 6-amino-6-desoxy-L-sorbose, by elimination, as a by-product. Further disadvantages of this procedure are the high production costs, which result from the use of platinum, and the formation of relatively large amounts (approximately 30%) of the isomeric 1,5-didesoxy-1,5-imino-L-iditol.

According to the present invention there are provided a process for the production of 1,5-didesoxy-1,5-imino-D-glucitol (desoxynojirimicin) or an N-derivative thereof of the formula

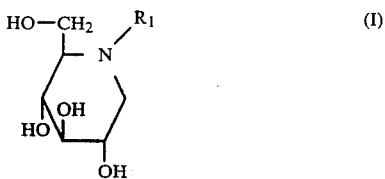

wherein
$R_1$ denotes a hydrogen atom or an optionally substituted alkyl, alkenyl, alkinyl or alkadienyl radical,
in which a compound of the formula

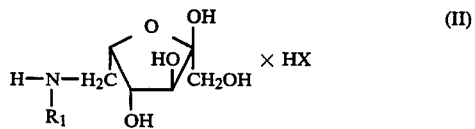

wherein
$R_1$ has the abovementioned meaining, and
HX is a strong inorganic or organic acid, is reduced with a complex borohydride.

$R_1$ preferably denotes an optionally substituted alkyl radical with 1 to 30, especially 1 to 18, carbon atoms, or an alkenyl radical, alkinyl radical or alkadienyl radical with 2 to 18, especially 2 to 10, carbon atoms.

The following may be listed as examples of substituents for alkyl: hydroxyl, alkoxy with 1 to 4 carbon atoms, acyloxy (the acyl radical thereof being derived from an aliphatic, particularly an alkane, carboxylic acids with 1 to 7 carbon atoms, an aromatic carboxylic acid, particularly phenylcarboxylic acid which is optionally substituted in the phenyl radical by one, two or more of hydroxyl, halogen, $C_1$ to $C_4$ alkyl, $C_1$ to $C_4$ alkoxy, nitro and amino, or a heterocyclic carboxylic acid derived from a 5-membered or 6-membered heterocyclic structure, which contains 1 to 3 hetero-atoms selected from N, O and S, and which is optionally substituted in the heterocyclic ring by $C_1$ to $C_4$ alkyl, chlorine, bromine or amino), amino, monoalkylamino and dialkylamino with preferably 1 to 4 carbon atoms in each alkyl radical, monoacylamino (acyl having the abovementioned meaning), mercapto, $C_1$ to $C_4$ alkylthio, halogen, $C_1$ to $C_4$ alkylcarbonyl, carboxyl, nitro, cyano, formyl, sulpho, heterocyclyl (as defined above for that part of the heterocyclic carboxylic acid), $C_3$ to $C_7$ cycloalkyl, and phenyl which is optionally substituted by halogen, $C_1$ to $C_4$ alkyl, $C_1$ to $C_4$ alkoxy, nitro, cyano or carboxyl.

Halogen is preferably fluorine, chlorine and bromine. Phthalimido, pyridinyl, thienyl, furyl, isoxazolyl, thiazolyl, glucopyranosyl, ribofuranosyl and oxiranyl are examples of heterocyclic structures in the abovementioned definitions.

The alkyl radicals $R_1$ are preferably unsubstituted, or substituted by substituent(s) selected from hydroxy, $C_1$ to $C_4$ alkoxy, mercapto, $C_1$ to $C_4$ alkylthio, halogen, nitro, amino, $C_1$ to $C_4$ alkylamino and $C_1$ to $C_6$ alkylcarbonylamino, the substituent(s) preferably not being located at the carbon atom adjacent to the ring nitrogen.

The strong acid HX in the general formula (II) is, for example, $H_2SO_4$, HCl or $HClO_4$. HX preferably represents hydrochloric acid. In principle, however, any strong acid which does not affect, in an undesired manner, the starting material, the reaction product and the reduction with the complex borohydride is suitable.

The reduction, which is carried out according to the invention with complex borohydrides, is carried out in an organic solvent or, preferably in water or a water-/organic solvent mixture. $C_1$ to $C_6$ alcohols (alkanols), preferably methanol, ethanol and isopropanol, are preferred solvents in this reduction. Ether or ether alcohols, such as ethylene glycol monomethyl ether or ethylene glycol dimethyl ether, can likewise preferably be employed. The borohydride used for the reduction, preferably $NaBH_4$, $NaBH_3CN$ or $HN(CH_3)_2 BH_3$, is generally added, before the actual reduction, to the solvent (or solvent mixture) in which the reduction is effected. In this process, a complex mixture of borohydrides is formed by reaction of the borohydride with the solvent, and individual hydride ions can be replaced by the alkyl ether radicals, alkyloxy ether radicals or alkoxy ether radicals from the solvent.

The amino sugar to be reduced may then be introduced into the reagent thus obtained.

Thereafter, the mixture is warmed for some time, advantageously for 30 to 150 minutes, preferably for approximately 1 hour, at a temperature from 60° to 100° C., preferably from 60° to 80° C.

It has proved advantageous to carry out the addition of the borohydride to the solvent (or solvent mixture) at a temperature of from −80° to 100° C., preferably, however, from 0° to 25° C. In addition, it is of advantage in the reduction carried out according to the invention if a basic auxiliary material is added to the initially introduced complex borohydride, the former being capable of binding the acid HX, and thereby reducing the quantity of borohydride employed. NaOH, KOH, $Na_2CO_3$ or organic bases, such as diethylamine or triethylamine, are examples of such basic auxiliary materials. The quantity of such basic auxiliary materials is advantageously the stoichiometric quantity, or somewhat above the stoichiometric quantity, which is necessary for binding the acid HX.

The molar ratio employed, between amino sugar and complex borohydride, should desirably be at least 1:0.25, in order to ensure a quantitative hydrogenation.

The isolation of the reaction product can be effected directly from the reaction solution which has been concentrated by evaporation, but, preferably, the reaction solution is demineralised by treatment with basic and, if necessary, with acid ion exchanger.

The corresponding desoxynojirimicins are obtained in very good yield and high purity.

Surprisingly, the reduction with the borohydride proceeds so sterospecifically that the undesired by-product (1,5-didesoxy-1,5-imino-L-iditol) could only be detected in the reaction mixture in trace amounts.

The following Examples illustrate the process according to the present invention.

EXAMPLE 1

Desoxynojirimicin (1,5-didesoxy-1,5-imino-D-glucitol)

50 g (0.23 mol) of 6-amino-6-desoxy-L-sorbose hydrochloride were dissolved in 500 ml of distilled water, and the solution was added in the course of one hour to a solution of 11.2 g of dimethylaminoborane in 500 ml of distilled water, whilst stirring at a temperature of 50° C. The mixture was stirred for one hour at room temperature and one hour at 50° C., 5 ml of triethylamine were added to it, and it was then poured over a column containing 800 ml of strongly basic ion exchanger ("Lewatit" MP 500 OH⁻-form). The exchanger was washed with distilled water, and the runnings collected were concentrated to a syrup on a rotary evaporator. The concentrated syrup was crystallised at 50° C., with addition of a large amount of ethanol. The suspension of crystals was cooled and filtered off under suction, and the crystalline product was dried in a vacuum drying cabinet.

Yield: 30 g≙80% of theory.

Melting point: 192° to 193° C.

EXAMPLE 2

Desoxynojirimicin (1,5-didesoxy-1,5-imino-D-glucitol) 25 g (0.115 mol) of 6-amino-6-desoxy-L-sorbose hydrochloride were dissolved in 200 ml of distilled water, and the solution was added at 5° C. to a mixture of 4.8 g of $NaBH_4$, 250 ml of ethanol/water 1:1 and 16.2 ml of triethylamine, whilst stirring. The mixture was further stirred for one hour at room temperature and one hour at 50° C., and the reaction mixture was poured over a column containing 400 ml of strongly basic ion exchanger ("Lewatit" MP 500 OH⁻-form). The exchanger was washed with distilled water, and the eluate collected was concentrated to a syrup in a rotary evaporator. Th syrup was taken up with 200 ml of distilled water, and the mixture was poured over a column containing 400 ml of acid ion exchanger ("Lewatit" S 100 H⁺-form). The column was rinsed with distilled water, and the product was eluted with 10% strength ammonia water. The runnings, rendered alkaline with ammonia, were collected and were concentrated to a syrup in a rotary evaporator. The syrup was crystallised, whilst warm, with a large amount of ethanol, and the suspension of crystals was cooled and is filtered off under suction, and the crystalline product was dried in a vacuum drying cabinet.

Yield: 14 g≙74% of theory.

Melting point: 192° to 193° C.

EXAMPLE 3

N-Hydroxyethyl-1-desoxynojirimicin 20 g (0.077 mol) of 6-[(2-hydroxyethyl)-amino]-6-desoxy-L-sorbose hydrochloride were dissolved in 200 ml of distilled water, and the solution was added dropwise in the course of 1 hour, at 5° C., to a solution of 4.5 g of dimethylaminoborane in 200 ml of distilled water, whilst stirring. The mixture was stirred for a further hour at room temperature, warmed for one hour to 50° C., and 2 ml of triethylamine were added to it, and the mixture was then poured over a column containing strongly basic ion exchanger ("Lewatit" MP 500 OH$^\ominus$-form). The exchanger was washed with distilled water, and the runnings collected were concentrated in a rotary evaporator. The syrup was crystallised, whilst warm, by addition of a large amount of ethanol. The crystalline product, which had been filtered off under sunction, was dried in a vacuum drying cabinet.

Yield: 9.7 g=61% of theory.

Melting point: 143° to 145.5° C.

What is claimed is:

1. A process for the production of 1,5-didesoxy-1,5-imino-D-glucitol or an N-derivative of the formula

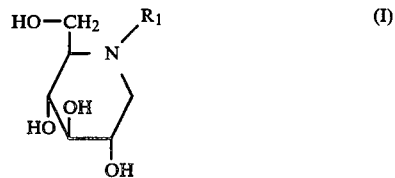

in which

R₁ denotes a hydrogen atom or an optionally substituted akyl, alkenyl, alkinyl or alkadienyl radical, or an acid addition salt thereof with the acid HX, which comprises reducing with dimethylamino borane, optionally in the presence of an auxiliary base, a compound of the formula

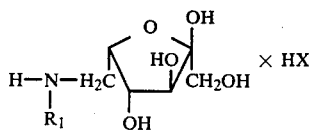 (II)

wherein

R₁ has the abovementioned meaning mentioned, and HX is a strong acid.

2. A process according to claim 1, in which the dimethylamino borane is a mixture of dimethylamino borane and water or water/organic solvent mixture.

3. A process according to claim 2, in which the organic solvent is a $C_1$ to $C_6$ alcohol or an ether or ether alcohol.

4. A process according to claim 3, in which the alcohol is methanol, ethanol or isopropanol.

5. A process according to claim 1, in which the reduction is carried out at a temperature from 60° to 100° C.

6. A process according to claim 5, in which the reduction is carried out at a temperature from 60° to 80° C.

7. A process according to claim 1, in which the molar ratio between the compounds of the formula (II) and the dimethylamino borane is at least 1:0.25.

8. A process according to claim 1, in which a basic auxiliary material for binding the acid HX is present in the reduction.

9. A process according to claim 8, in which the basic auxiliary material is NaOH, KOH, $Na_2CO_3$, diethylamine or triethylamine.

* * * * *